United States Patent
Lorca et al.

(10) Patent No.: US 12,194,066 B2
(45) Date of Patent: Jan. 14, 2025

(54) MECHANISTIC BACTERIAL EFECTOR TO PREVENT APOPTOSIS OF HUMAN BETA CELLS

(71) Applicant: UNIVERSITY OF FLORIDA RESEARCH FOUNDATION, INCORPORATED, Gainesville, FL (US)

(72) Inventors: Graciela Liliana Lorca, Gainesville, FL (US); Claudio F. Gonzalez, Gainesville, FL (US)

(73) Assignee: UNIVERSITY OF FLORIDA RESEARCHFOUNDATION, INCORPORATED, Gainesville, FL (US)

( * ) Notice: Subject to any disclaimer, the term of this patent is extended or adjusted under 35 U.S.C. 154(b) by 1011 days.

(21) Appl. No.: 17/059,586

(22) PCT Filed: May 30, 2019

(86) PCT No.: PCT/US2019/034507
§ 371 (c)(1),
(2) Date: Nov. 30, 2020

(87) PCT Pub. No.: WO2019/232122
PCT Pub. Date: Dec. 5, 2019

(65) Prior Publication Data
US 2021/0205379 A1    Jul. 8, 2021

Related U.S. Application Data

(60) Provisional application No. 62/677,785, filed on May 30, 2018.

(51) Int. Cl.
A61K 35/747    (2015.01)
A61P 3/10    (2006.01)

(52) U.S. Cl.
CPC .............. *A61K 35/747* (2013.01); *A61P 3/10* (2018.01)

(58) Field of Classification Search
None
See application file for complete search history.

(56) References Cited

U.S. PATENT DOCUMENTS

2013/0195765 A1    8/2013    Gho et al.

FOREIGN PATENT DOCUMENTS

| WO | 2017187190 A1 | 11/2017 |
|---|---|---|
| WO | 2019051380 A1 | 3/2019 |

OTHER PUBLICATIONS

Raskin et al. (2004) Current Pharmaceutical Design 10, 3419-3429. (Year: 2004).*
Lau et al. (2011) J. Immunology. 186(6): 3538-3546. (Year: 2011).*
Valladares, Ricardo et al., "Lactobacillus johnsonii N6.2 Migigates the Development of Type 1 Daibetes in BB-DP Rats", PLoS ONE, May 2010, vol. 5, issue 5, e10507, 9 pages.
PCT/US2019/034507, PCT Search Report & Written Opinion, Nov. 5, 2019, 11 pages.
Kingma, Sandra D. et al., "Lactobacillus johnsonii N6.2 Stimulates the Innate Immune Response through Toll_like Receptor 9 in Caco-2 Cells and Increases Intestinal Crypt Paneth Cell No. in BioBreeding Diabetes-Prone Rats", American Society for Nutrition, 2011, pp. 1023-1028.
Grande, Rossella et al., "Detection and Physicochemical Characterization of Membrane Vesicles (MVs) of Lactobacillus reuteri DSM 17938", Frontiers in Microbiology, Jun. 2017, vol. 8, article 1040, 10 pages.
Al-Nedawi, Khalid et al., "Gut commensal microvesicles reproduce parent bacterial signals to host immune and enteric nervous systems", The FASEB Journal, May 1, 2018, vol. 29, No. 2, pp. 684-695.
Smythies, Lesley E. et al., "Exosomes in the gut", Frontiers in Immunology, Mar. 2014, vol. 5, article 104, pp. 1-4.
Schorey, Jeffrey S et al., "Exosomes and other extracellular vesicles in host-pathogen interactions", EMBO reports, 2015, vol. 16, No. 1, pp. 24-43.
Perez-Burgos, Azucena et al., "Psychoactive bacteria Lactobacillus rhamnosus (JB-1) elicits rapid frequency facilitation in vagal afferents", Am J Physiol Gastroinest Liver Physiol, 2013, vol. 304, pp. G211-G220.
Yuana, Yuana et al., "Extracellular vesicles in physiological and pathological conditions", Blood Reviews , 2013, vol. 27, pp. 31-39.

* cited by examiner

*Primary Examiner* — Russell G Fiebig
(74) *Attorney, Agent, or Firm* — Timothy H. Van Dyke; Wolter Van Dyke Davis, PLLC

(57) ABSTRACT

A composition is provided herein, including microvesicles (MVs) isolated from a naturally occurring probiotic *Lactobacillus* sp. wherein the MVs are packaged in a capsule, emulsion, or tablet such that the packaged MVs are protected in a gastrointestinal tract for transport to an intestine of a subject. In another embodiment, a method for treating Type-1 diabetes including orally administering to a diabetic or pre-diabetic subject, or a subject at risk for becoming pre-diabetic or diabetic, a composition comprising an effective amount of microvesicles isolated from a naturally occurring probiotic strain comprising a *Lactobacillus* sp.i. In still a further embodiment, of improving immune function in a subject, comprising administering to the subject, the composition comprising an effective amount of microvesicles isolated from a naturally occurring probiotic *Lactobacillus* sp.

5 Claims, 1 Drawing Sheet

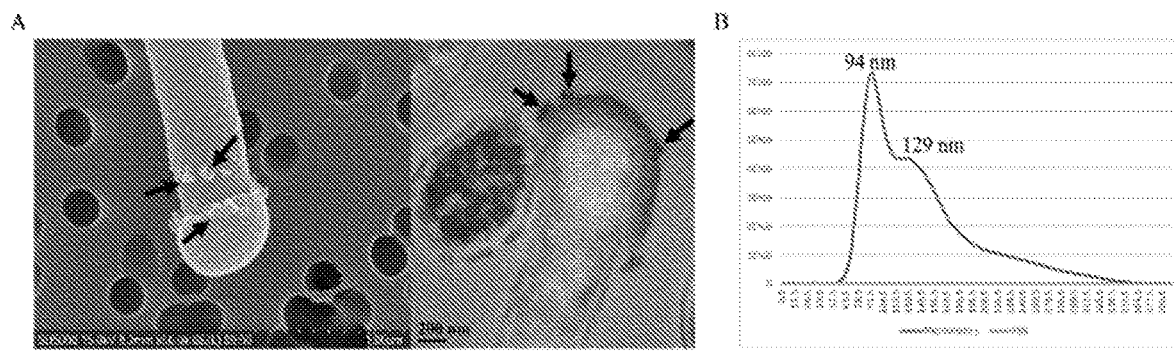
Figure 1. A, Transmission (left) and scanning (right) electron microscope images of LJ's budding vesicles identified with black arrows. B, Nanosight data showing two major peak sizes (94 and 129 nm) of microvesicles shown in blue.
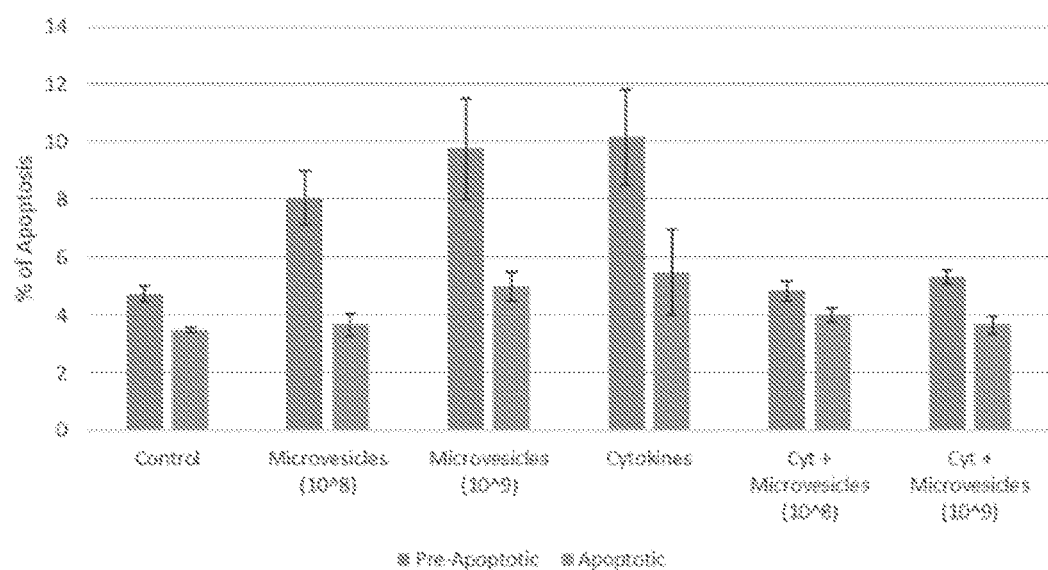
Figure 2

MECHANISTIC BACTERIAL EFECTOR TO PREVENT APOPTOSIS OF HUMAN BETA CELLS

GOVERNMENT SUPPORT STATEMENT

This invention was made with government support under Grant No. 2015-67017-23182 awarded by United States Department of Agriculture. The government has certain rights in the invention.

BACKGROUND

Type 1 diabetes is an autoimmune disease that affects blood sugar regulation. In type-1 diabetes, a person's immune system makes antibodies that destroy the insulin-producing islet beta cells in the pancreas. As a result, the pancreas fails to make insulin. Without insulin, blood sugar increases and cannot be delivered to the muscles and brain where it is needed. Over time, high blood sugar can lead to a number of complications including kidney, nerve, and eye damage, and cardiovascular disease. Moreover, cells do not receive the glucose necessary for energy and normal function. Because people with type 1 diabetes can no longer produce their own insulin, they must inject doses of insulin. They must match the amount of insulin they inject with their diet. Keeping blood sugar in a normal, healthy range (what doctors call "good glycemic control") is the key to preventing long-term deteriorating effects, including as heart disease, diabetic neuropathy, kidney disease, or poor wound healing resulting from high blood glucose levels over a prolonged time period.

BRIEF DESCRIPTION OF DRAWINGS

FIG. 1A shows a scanning and transmission electron microscope images evidencing the presence of extracellular microvesicles.

FIG. 1B is a graphical representation of concentration and size of nanoparticles of EMVs produced by *L. johnsonii* following ultracentrifugation of *L. johnsonii* grown supernatant was performed and analysis of the pellet using NanoSight (NS300) technology.

FIG. 2 is a graphical illustration of a study, wherein human pancreatic beta cells, treated with cytokines and microvesicles were evaluated to determine the differences in the apoptotic affects of each treatment, and percentage of apoptosis is displayed.

DETAILED DESCRIPTION

As disclosed herein, *L. johnsonii* produces extracellular vesicles that mediate beneficial interactions between the bacteria and the subject into which they are administered. This interaction typically occurs in the gastrointestinal tract (GI) of the subject. Based on the discoveries summarized herein, a composition including microvesicles (MVs) isolated from a naturally occurring probiotic *Lactobacillus* species is provided. In a related embodiment, the composition containing the MVs is used for the treatment of a diabetic or pre-diabetic subject, or a subject at-risk for diabetes. In a preferred embodiment, the diabetes comprises type-1 diabetes (T1D). In a further embodiment, the *Lactobacillus* strain includes *Lactobacillus johnsonii*. In still a further embodiment, the *Lactobacillus johnsonii* strain comprises *Lactobacillus johnsonii* N6.2. In one example, the MVs decrease a proinflammatory response in human pancreatic beta cells (HPB). Without being bound to any theory, it is believed that the MVs inhibit apoptotic and/or pre-apoptotic human pancreatic beta cells in the subject.

The composition may be formulated by methods known to those skilled in the art. In one embodiment, the composition including microvesicles isolated from *L. johnsonii* packaged within a pharmaceutically acceptable vehicle, such as a capsule, suppository, tablet or microemulsion.

In another embodiment, a pharmaceutical composition including microvesicles (MVs) isolated from a naturally occurring probiotic *Lactobacillus johnsonii* strain, optionally packaged in a pharmaceutically-acceptable vehicle, or combined with a pharmaceutically-acceptable carrier, or excipient, is provided. In a further embodiment, the microvesicles may be isolated from *Lactobacillus johnsonii*.

In a further embodiment, treatment is administered prior to the onset of clinical manifestation of type 1 diabetes. The time of administration is preferably before extensive irreversible beta cell destruction as evidenced by, for example, the clinical onset of type 1 diabetes. Consequently, in at least one embodiment, treatment is administered to a subject in a pre-diabetic state. In at least another embodiment, treatment is administered to a subject at risk for diabetes. In another embodiment, treatment is administered to a subject in a diabetic state to deter or prevent further damage to the HPB cells in the subject.

In addition, a method is provided wherein the subject exhibits a cytokine-induced pro-inflammatory response, the composition inhibits apoptosis of beta cells.

In yet further embodiments, methods for improving immune function in a subject are provided, including administering to the subject, a composition or pharmaceutical composition including microvesicles (MVs) isolated from a naturally occurring probiotic *Lactobacillus* species is provided. In a further embodiment, the *Lactobacillus* species pertains to *Lactobacillus johnsonii*. In still a further embodiment, the *Lactobacillus johnsonii* pertains to the *Lactobacillus johnsonii* N6.2 strain.

The method may further include administering the composition to increase expression of Toll like receptor 7 (TLR7) and Toll like receptor 9 (TLR9) in the subject. The method may further include a composition comprising microvesicles from whole *Lactobacillus johnsonii* cells, from cell-free extracts, or from pure nucleic acids.

Overview

Type 1 diabetes can affect many major organs, including heart, blood vessels, nerves, eyes and kidneys leading to cardiovascular diseases, retinopathy (up to blindness), neuropathy and nephropathy (up to dialysis). Adequate control of blood glucose concentration can dramatically reduce the risk of many complications. The main treatment regimen for type 1 diabetes involves administration of insulin, usually subcutaneously. There are different regimens for insulin therapy, and various combinations of long acting, intermediate and short acting insulins can be used depending on the context. Continuous insulin delivery using a pump can also be used to control blood glucose concentration. The more intensive regimens tend to provide better control of blood glucose, however they are much more intrusive to the patient's life, which can be a particular problem when treating juveniles with this condition. Type 1 diabetes mellitus is typically called "juvenile diabetes" due to its early onset. Risk factors for Type 1 diabetes includes a family history of Type-1 diabetes, introducing certain foods too early (fruit), or too late (oats/rice), and exposure to toxins.

In view of the unsatisfactory prognosis for patients with type 1 diabetes, it would be advantageous to have an alternative treatment which could be used instead of insulin. In particular, it would be especially advantageous to have a treatment able to delay the onset of type 1 diabetes or slow down its progression, especially at early stages, where beta cells destruction has not reached the critical point yet. It has been discovered herein that microvesicles (MVs), also called extracellular microvesicles (EMVs), from a particular microorganism, *Lactobacillus johnsonii*, were efficient at protecting beta cells from cellular death, and could consequently be useful in the treatment of type 1 diabetes. This would help to prevent further beta cell death once the diagnosis of type 1 diabetes has been performed, or to try to preserve beta cell mass not yet impacted by apoptosis via the autoimmune process. Further, use of these microvesicles from *L. johnsonii* may be used to prevent or delay beta cell death in at risk population before the stage of type 1 diabetes, for instance in relatives of type 1 diabetes subjects with positive antibodies, or to possibly regenerate beta cells in the pancreas.

*L. johnsonii* N6.2 has been shown to mitigate the development of type-1 diabetes in BioBreeding diabetes prone (BB-DP) rats. The administration of the bacteria resulted in improvements of the intestinal epithelial barrier, increasing mucus production and tight junction proteins, while reducing reactive oxygen species effects. *L. johnsonii* has been discovered herein to target an inflammatory signaling pathway creating a tolerogenic environment allowing for the reduction of oxidative stress. The effects of *L. johnsonii* have been observed on human intestinal epithelial cells to determine the Toll-like receptor (TLR) signaling pathways and their effects on the innate immune response. Using whole cells, *L. johnsonii* cell-free extracts and pure nucleic acids, an increased expression of TLR7 and TLR9 (both involved in nucleic acid sensing) has been observed, demonstrating that *L. johnsonii* utilizes DNA and/or RNA as its main signaling component. Extracellular vesicles from both eukaryotes and prokaryotes are associated with the delivery of cargo DNA, RNA or proteins. Furthermore, vesicles contain other components such as other metabolic compounds and structural components such as lipids. Extracellular vesicles, particularly, microvesicles (MV) identified in transition/scanning electron images of *L. johnsonii* were shown herein to facilitate an interaction with a host systemically by interacting with human pancreatic beta-cells (HPB) known to be responsible for insulin production.

Definitions

The terms "pre-diabetic," "pre-diabetes," "pre-diabetic state," or "pre type-1 diabetes," as used herein refers to a subject at risk for diabetes, and in particular, a subject at risk for type-1 diabetes. For example, a pre-diabetic patient or subject may have a fasting blood sugar level between 100 and 125 mg/dL.

The term "diabetic state," or "diabetes" as referred to herein refers to a state in which the blood sugar level reaches at least 126 mg/dL, in one example. Symptoms of Type 1 diabetes include frequent urination, excess thirst, weight loss (often sudden), skin infections, bladder/vaginal infections, and abdominal pain. Diabetes may be diagnosed with a blood test, which measures blood sugar level, and also measures levels of insulin and antibodies to confirm the diagnosis.

The term "microvesicle" or "MV(s)" as used herein refers generally to any plasma membrane bound particle, that may reside within the cell, or in the extracellular environment. These structures are not limited in any way with regard to in vivo localization (e.g., intracellular or extracellular), in a body fluid, in a cell culture media, generated by in vitro cultured cells, mechanism of origin or size characteristics. In some embodiments, a microvesicle can range in size with a lower size limit of at least about 20 nanometers (nm) in diameter, or alternatively, 30 nm, or 40 nm, or 50 nm in diameter. In some embodiments, a microvesicle has an upper size limit of not more than about 1,000 nm (i.e., 1.0 micrometer, micron, or µm), or alternatively, not more than about 1,500 nm, about 2,000 nm or about 2,500 nm. Microvesicles include, but are not limited to, particles such as shedding microvesicle, exosomes, epididimosomes, argosomes, and apoptic body.

As used herein, the term "shedding microvesicle (SMV)" refers to a class of microvesicles that are produced by cells using a mechanism of direct plasma membrane budding, fission and shedding to produce microvesicles that are released by a cell into an extracellular environment. For example, SMVs can be produced by (i) exocytosis from multivesicular bodies to produce exosomes, (ii) budding, fission and shedding of microvesicles directly from a cytoplasmic membrane, and (iii) membranous blebs caused by programmed cell death leading to the formation of apoptotic bodies. As used herein, it is not intended that an SMV of the invention be limited by any particular size or size range.

As used herein, the term "exosome" refers to a subset of circulating microvesicles that are preformed microvesicles that are released from the cell following the exocytic fusion of intracellular multivesicular bodies with the plasma membrane, i.e., exosomes have an endocytic origin. As used herein, it is not intended that an exosome of the invention be limited by any particular size or size range.

As used herein, the term "apoptotic body" refers to a subset of circulating microvesicles that are produced as a result of apoptotic cell destruction. As used herein, it is not intended that an apoptotic body of the invention be limited by any particular size or size range.

As used herein, by the term "effective amount," "amount effective," "therapeutically effective amount," or the like, it is meant an amount effective at dosages and for periods of time necessary to achieve the desired result. These terms refers to an amount of an enumerated agent, which, when administered or co-administered in a proper dosing regimen, is sufficient to reduce or ameliorate the severity, duration, or progression of the disorder being treated (e.g., type 1 diabetes), prevent the advancement of the disorder being treated (e.g., type 1 diabetes), cause the regression of the disorder being treated (e.g., type 1 diabetes), or enhance or improve the prophylactic or therapeutic effects(s) of another therapy. The full therapeutic effect does not necessarily occur by administration of one dose and may occur only after administration of a series of doses. Thus, a therapeutically effective amount may be administered in one or more administrations per day for successive days.

The terms "treat", "treating" or "treatment of" as used herein refers to providing any type of medical management to a subject. Treating includes, but is not limited to, administering a composition to a subject using any known method. for purposes such as curing, reversing, alleviating, reducing the severity of, inhibiting the progression of, or reducing the likelihood of a disease, disorder, or condition or one or more symptoms or manifestations of a disease, disorder or condition.

Microvesicles

As noted above, microvesicles can be formed by a variety of processes, including the release of apoptotic bodies, the budding of microvesicles directly from the cytoplasmic membrane of a cell, and exocytosis from multivesicular bodies. For example, exosomes are commonly formed by their secretion from the endosomal membrane compartments of cells as a consequence of the fusion of multivesicular bodies with the plasma membrane. The multivesicular bodies (MVBs) are formed by inward budding from the endosomal membrane and subsequent pinching off of small vesicles into the luminal space. The internal vesicles present in the MVBs are then released into the extracellular fluid as so-called exosomes.

As part of the formation and release of microvesicles, unwanted molecules are eliminated from cells. However, cytosolic and plasma membrane proteins are also incorporated during these processes into the microvesicles, resulting in microvesicles having particle size properties, lipid bilayer functional properties, and other unique functional properties that allow the microvesicles to potentially function to carry their payload.

According to one embodiment, microvesicles are isolated from a naturally occurring probiotic *Lactobacillus* sp. In a specific embodiment, the *Lactobacillus* species is *Lactobacillus johnsonii*. In an even more specific embodiment, microvesicles are isolated from a strain of *Lactobacillus johnsonii*, *Lactobacillus johnsonii* N6.2 As used herein, the term "isolating," or "to isolate," refers to any artificial (i.e., not naturally occurring) process for treating a starting material, where the process results in a more useful form of a molecule or structure of interest that is in the starting material. The "more useful form" of the molecule or structure of interest can be characterized in a variety of ways, no one of which is limiting. For example, as used herein, the invention provides methods for isolating microvesicles from a sample containing a *Lactobacillus* sp. Further, for example, the process for isolating can result in:

(i) the molecule of interest having a greater concentration in the isolated form compared to the starting material (e.g., concentrating), (ii) the removal of any amount or any type of impurities from the starting material (e.g., purifying), (iii) an increase in the ratio of the amount of molecule of interest to the amount of any undesired component in the starting material (e.g., enriching), (iv) any artificial process for removing a molecule or structure of interest from its natural source or location;

(v) any artificial process for separating a molecule or structure of interest from at least one other component with which it is normally associated (e.g., purifying), or (vi) any combination of (i), (ii), (iii), (iv) or (v).

Similarly, as used herein, the term "isolated" generally refers to the state of the molecule or structure of interest after the starting material has been subjected to a method for isolating the molecule of interest. That is to say, isolating a molecule of interest from a starting material will produce an isolated molecule. For example, the methods of the invention are used to produce preparations of isolated microvesicles. These preparations of microvesicles have been isolated from their natural source, for example, from urine, or from conditioned cell culture media.

As used herein, the term "purifying" or "to purify" a molecule or structure of interest refers to a process for removing at least one impurity or contaminant from a starting material. For example, purifying a molecule of interest from a starting material refers to a process for removing at least one impurity from the starting material to produce a relatively more pure form of the molecule of interest.

As used herein, the term "substantially purified" refers to molecules or structures of interest that are removed from their natural environment or from a starting material (i.e., they are isolated) and where they are largely free from other components with which they are naturally associated or substantially free of other components that may render future use or study sub-optimal, difficult or impossible.

As used herein, the terms "purified" or "partially purified" refers to molecules or structures of interest that are removed from either (1) their natural environment, or from (2) a starting material (i.e., they are isolated), and where (a) at least one impurity from the starting material has been removed, or (b) at least one component with which the molecule is naturally associated has been removed. A "purified" or "partially purified" molecule may still contain additional components that may render future use or study of the molecule sub-optimal, difficult or impossible.

As used herein, the term "enriching" (and "enriched" and the like) refers to a process whereby a molecule of interest that is in a mixture has an increased ratio of the amount of that molecule to the amount of other undesired components in that mixture after the enriching process as compared to before the enriching process.

As used herein, the term "concentrating" refers to a process whereby a molecule or structure of interest that is in a mixture that has been subjected to that process has a greater concentration after the process as compared to the concentration of the molecule in the mixture before the process.

As used herein, the term "depleted" refers to a mixture containing an undesirable component, where that undesirable component has been (i) completely removed from the mixture, (ii) sufficiently removed from the mixture to be undetectable, or (iii) partially removed from the mixture such that its concentration in the mixture is significantly reduced. For example, a sample that has been depleted of endogenous microvesicles may contain no microvesicles, or may contain no detectable microvesicles, or may contain a reduced level of microvesicles compared to the untreated sample.

In a specific embodiment, microvesicles from *Lactobacillus* sp. such as *Lactobacillus johnsonii* are isolated by subjecting a media sample comprising the *Lactobacillus* sp. to centrifugation.

Compositions

Embodiments of the present invention include pharmaceutical compositions comprising microvesicles isolated from *Lactobacillus* sp, such as *Lactobacillus johnsonii*. Such pharmaceutical compositions comprise a therapeutically effective amount of microvesicles, and a pharmaceutically acceptable carrier. In a specific embodiment, the term "pharmaceutically acceptable" means approved by a regulatory agency of government or listed in the US Pharmacopeia, the European or UK Pharmacopeia or other generally recognized pharmacopeia for use in animals, and more particularly in humans. The term "carrier" refers to a diluent, adjuvant, excipient, or vehicle with which the microvesicles are administered. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin. Such compositions will contain a therapeutically effective amount of the microvesicles, preferably in purified form, together with a suitable amount of carrier so as to provide the form for proper administration to the patient. The formulation should suit the mode of administration.

One or more other excipients may be included in the composition of this invention to (1) impart satisfactory processing and compression characteristics to the composition (e.g., adjust the flowability, cohesion and other characteristics of the composition) and (2) give additional desirable physical characteristics to the tables (e.g. color, stability, hardness, disintegration). Mostly the excipients aid in the delayed release of the drug from the composition to achieve regional delivery to the lower GI. As used herein, the term "excipient" may include all excipients present in the dosage form, including all components other than the drug entity and the hydrocolloid gum from higher plants. A plurality of excipient substances may be present in any dosage form, and may include multiple substances having similar pharmaceutical function (e.g., lubricants, binders, diluents) or similar structure (e.g., a mixture of monosaccharides). Preferably the fewer excipients present the better. Such excipients are present in an amount sufficient to provide the composition with the desired delayed release/regional delivery characteristics, hardness rating and handling characteristics and will generally be present at a level of about 2% by weight to about 50% by weight, preferably about 2% by weight to about 40% by weight and more preferably about 2% to about 10% by weight. Excipients may be selected from many categories known in the pharmaceutical arts. The excipients used will be chosen to achieve the desired object of the invention keeping in mind the activity of the drug being used, as well as its physical and chemical characteristics such as water solubility and possible interactions with the excipients to be used.

For example with drugs that are more water soluble, generally a lower percentage by weight of excipients will be used, i.e., less than about 20% or from about 2% to about 15% by weight, preferably no more than about 10% by wt, while for drugs that are less water soluble a higher percentage by weight may be used, e.g., about 20% up to about 40% by wt. These levels may be adjusted to achieve the desired hardness and porosity of the final tablet composition to obtain the delayed release profile.

From the foregoing discussion, it is seen that one aspect of this invention is a particle mass of a solid dosage form that can be administered orally as a tablet. Thus, the composition is neither a liquid nor a gas, but a solid tablet having an amount of drug as a unit dosage. Generally, this unit dosage will be an amount that can be swallowed by a human subject and may vary from a total of about 100 milligrams to about 1500 mg, preferably no more than about 1200 mg and particularly no more than about 800 mg. For children, the size of the tablet may be significantly less than for adults, and for elderly patients who have difficulty swallowing, the total amount may be less than what would be viewed as a normal amount for adults. It is to be understood that the tablets of this invention may be designed as a single tablet having a unit dosage amount or several smaller tablets, e.g. 2-5, may be combined in a capsule for oral administration. The composition used to prepare the tablet may be granulated.

In a preferred embodiment, the pharmaceutical composition is formulated in accordance with routine procedures as a pharmaceutical composition adapted for oral administration to humans.

The amount of the *Lactobacillus* sp. microvesicles which will be effective in the treatment of a particular disease or disorder will depend on the nature of the disease or disorder, and can be determined by standard clinical techniques. In addition, in vitro and in vivo assays may optionally be employed to help identify optimal dosage ranges. The dosage will depend on the body weight of the subject. However, in one example suitable dosage ranges for oral administration or parenteral administration may be about 10 pg to 100 mg, 20 pg to 50 mg, 0.1 mg to 20 mg, or 0.5 mg to 10 mg (calculated either per kg body weight or as total dose per individual). Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain an active ingredient in the range of 0.5% to 10% by weight; oral formulations preferably contain 10% to 95% active ingredient.

One aspect of this invention is an orally-deliverable tablet having an inner composition optionally surrounded by a pharmaceutically-acceptable coating. The tablet preferentially delivers a therapeutically effective amount of a composition comprising microvesicles (MVs) isolated from a naturally occurring probiotic *Lactobacillus* sp. to the GI tract downstream from the stomach, without significant release of the composition in the stomach upon oral administration of the composition to a subject in need thereof. The composition or pharmaceutical composition of the invention can be coated with an enteric coating. The MVs can be provided in a tablet or capsule and can be released in a burst or in a controlled fashion. The MVs can also be encapsulated in a microsphere, a liposome, a nanosphere or a microemulsion, or be provided in the form of pellets or minitablets for delivery to and release in the intestine.

The general approaches to delivering drugs to the lower GI tract (e.g. small intestine and colon) for interaction with immune cells in the mucosa of the lower GI tract include: 1) enteric coating designed to release drug in the more alkaline environment of the gastrointestinal tract, 2) bioerodible coatings and matrices, 3) prodrugs, 4) timed-release systems and, 5) enteric polymeric material-based release systems that release drug after they transit through the stomach and reach the intestines. A general discussion of these approaches and others may be found in PCT Patent application No. PCT/US91/03014 by Sintov and Rubinstein.

Process of Preparation

Capsules containing microvesicles can be prepared according to known techniques. See for example US Pat. Pub. 20170368049 incorporated by reference. For preparing solid compositions such as tablets, the principal active ingredient may be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the intestine or lower GI tract, or to otherwise be delayed in release. A variety of materials can be used for such enteric layers or coatings, such materials including a number of polymeric acids and mixtures of polymeric acids with such materials as shellac, acetyl alcohol and cellulose acetate.

In preparing the tablet compositions of this invention one may use pharmaceutical compression or molding techniques, preferably the former due to its adaptability to large scale production methods. Using techniques known in the art, the tablets of the invention may take any appropriate shape such as discoid, round, oval, oblong, cylindrical, triangular, hexagonal, and the like. The tablets may be coated or uncoated. If coated they may be sugar-coated (to cover objectionable tastes or odors and to protect against oxidation), film coated (a thin film of water soluble matter for similar purposes), or enteric coated (to resist dissolution in gastric fluid but allow disintegration of the coating in the small intestine—as discussed herein before). Depending on whether the tablet is a uniform matrix tablet, an active core tablet or a concentration gradient tablet, the process for preparation will vary slightly.

In order to ensure tablet hardness and uniformity of weight, content and other items, it is preferable to prepare the tablets having the composition of this invention by using a pre-granulation technique. In general, the granulation techniques can include the wet granulation method, the fluid bed granulation method, the dry granulation method or direct compression.

Once the tablets are appropriately formed, they can then be coated by any of the necessary coating techniques as discussed in Chapter 90 of Remington's. For example, the tablets may be sugar-coated in accordance with the procedure discussed therein or film coated or preferably enterically coated. Enteric coating is preferred in the tablets of this invention to minimize the release of any of the drug in the upper GI and assure the release to the lower GI particularly the colon. As much as pertinent of the Remington's sections of Chapters 88 and 90 is incorporated herein by reference.

Administration

In some embodiments, the composition embodiments comprising MVs described herein will be administered orally to a mammalian subject in need thereof using a level of pharmaceutical composition that is sufficient to provide the desired physiological effect. The mammalian subject may be a domestic animal or pet but preferably is a human subject. The level of pharmaceutical composition needed to give the desired physiological result is readily determined by one of ordinary skill in the art. Other parameters that may be taken into account in determining dosage for the pharmaceutical composition embodiments described herein may include disease state of the subject or age of the subject.

The compositions may take the form of suspensions, solutions or emulsions in oily or aqueous vehicles and may contain formulatory agents such as suspending, stabilizing and/or dispersing agents. In some embodiments, the composition embodiments described herein may be administered orally or intravenously via parenteral nutritional therapy to a subject via an emulsion. The emulsion may include, in some embodiments, an aqueous continuous phase and a dispersed phase. The boundary between the phases called the "interface". The present emulsions are adapted for application to a mucosal surface of a vertebrate animal, preferably a mammal, including humans. These compositions improve the permeability and bioavailability of active compounds after application to a mucous surface. Mucosal surfaces of interest include the intestinal mucosa. Use of bioadhesive polymers in pharmaceutical emulsions affords enhanced delivery of drugs in bioadhesive polymer-coated suspensions, in some examples. Bioadhesive pharmaceutical emulsions may be used to deliver the MVs isolated from *Lactobacillus* sp. described herein to: a) prolong the residence time in situ, thereby decreasing the number of drug administrations required per day; and b) may be localized in the specified region to improve and enhance targeting and bioavailability of delivered drugs.

The ability to retain and localize a drug delivery emulsion in a selected region leads to improved bioavailability, especially for drugs exhibiting a narrow window of adsorption due to rapid metabolic turnover or quick excretion. Intimate contact with the target absorption membrane improves both the extent and rate of drug absorption.

Bioadhesion is the characteristic of certain natural and synthetic polymers of binding to various biological tissues. Of particular interest are polymers which bind to the mucous lining that covers the surface of many tissues which communicate directly or indirectly with the external environment, such as the gut, for example. Mucus binding polymers may be referred to as mucoadhesive. Several bioadhesive, and specifically mucoadhesive, polymers are known. The chemical properties of the main mucoadhesive polymers are summarized as follows:

a. strong H-bonding groups (—OH, —COOH) in relatively high concentration;
b. strong anionic charges;
c. sufficient flexibility of polymer backbone to penetrate the mucus network or tissue crevices;
d. surface tension characteristics suitable for wetting mucus and mucosal tissue surfaces; and
e. high molecular weight.

Bioadhesive polymers may be used in the pharmaceutical composition embodiments described herein, examples of bioadhesive polymers currently used in pharmaceutical preparations include: carboxymethylcellulose (CMC), hydroxypropylmethylcellulose (HPMC), polyacrylic and polymethacrylic acid and their derivatives, pectin, alginic acid, chitosan, polyvinylpyrrolidone, hyaluronic acid, and polyvinyl alcohol. The most frequently used polymer is Carbopol (Carbomer), which is a high molecular weight polyacrylic acid polymer. It is used in many formulations for bioadhesive drug delivery systems, as a suspending agent, as a tablet coating, and in ocular suspensions.

Pharmaceutical composition embodiments described herein may include the composition comprising MVs isolated from *Lactobacillus* sp. incorporated into inert lipid carriers such as oils, surfactant dispersions, emulsions, liposomes etc. Self-emulsifying formulations are ideally isotropic mixtures of oils, surfactants and co-solvents that emulsify to form fine oil in water emulsions when introduced in aqueous media. Fine oil droplets would pass rapidly from stomach and promote wide distribution of drug throughout the GI tract, thereby overcome the slow dissolution step typically observed with solid dosage forms. These embodiments may provide control release self-emulsifying pellets, microspheres, tablets, capsules etc. that increase the use of "self-emulsification.".

In further embodiments, composition embodiments described herein may be microencapsulated for delivery to a subject. Microencapsulation (ME) offers the potential to reduce the adverse effects on probiotic viability in the gastrointestinal (GI) tract environment. ME separates microorganism cells from their environment until they are released. Controlled release of the MV's is a particular benefit of ME. It is beneficial for encapsulated probiotic microorganisms to be released in the small intestine where the Peyer's patches exist to activate the immune system, in some embodiments.

Oral delivery will be the most straightforward mode of administration to deliver the microvesicles to the gut mucosa. However, in alternative embodiments, other methods of administration are contemplated. Accordingly, suitable methods for administering a microvesicle containing composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, dermally (e.g., topical application), intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments of the therapeutic methods described herein, the therapeutic compositions are administered orally, intravenously, intranasally, or intraperitoneally to thereby treat a disease or disorder.

Regardless of the route of administration, the compositions of the presently-disclosed subject matter typically not only include an effective amount of a microvesicles, but are typically administered in amount effective to achieve the desired response. As such, the term "effective amount" is used herein to refer to an amount of the therapeutic composition (e.g., a microvesicles, and a pharmaceutically vehicle, carrier, or excipient) sufficient to produce a measurable biological response (e.g., a decrease in diabetes symptoms or increase in immune function). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

Examples

Materials and Methods

*Lactobacillus johnsonii* cultures were inoculated in ultracentrifuged, filter-sterilized MRS media (glucose 20 g, peptone 10 g, meat extract powder 10 g, yeast peptone 5 g, $K_2HPO_4$ 2 g, sodium acetate 5 g, ammonium citrate tribasic 2 g, $MgSO_4 \cdot 7H_2O$ 0.2 g, $MnSO_4 \cdot H_2O$ 0.05 g, and Tween-80 1 g raised to a final volume of 1 L with distilled water, pH=6.5±0.2) for 12 h. The resulting cultures were spun down at low speed and the supernatant was ultracentrifuged to retrieve MV. Crude MV samples were analyzed using Nanosight technology based on light scattering and Brownian motion to determine size and concentration. Proteomics was used to compare the protein composition of *Lactobacillus johnsonii* cell membrane (CM) and MV. CM was recovered after cell lysis and biological replicates of CM and MV pellets were loaded on SDS-PAGE and subjected to LC-MS/MS. To test for the reduction of proinflammatory responses and limit cell apoptosis, human pancreatic beta-cells (HPB) were exposed to MV both with and without exposure to cytokines.

Results

*L. johnsonii* N6.2 Produce Microvesicles

Small protrusions budding off *L. johnsonii* on scanning and transmission electron microscope images evidence the presence of extracellular microvesicles (EMVs) (FIG. 1A). To identify EMVs produced by *L. johnsonii*, ultracentrifugation of *L. johnsonii* grown supernatant was performed and the pellet was analyzed using NanoSight (NS300) technology, detecting the concentration and size of nanoparticles. The total concentration of EMVs is $5.85 \times 10^{11}$ with $4.94 \times 10^{11}$ (~84%) lying within the 20-200 nm range of known vesicle sizes for other bacterial species and resulting in two major peak sizes of 94 and 128 nm in size (FIG. 1B).

*L. johnsonii* N6.2 Microvesicles Prevents Apoptosis in Beta Cells

Stemming from the research showing *L. johnsonii* mitigating the onset of type-1 diabetes in diabetes prone rats, it was first identified herein that MVs facilitate an interaction with the host systemically through the interaction of, responsible for insulin production. A study of beta-cell lines treated with microvesicles showed the reduction of apoptotic cells when a proinflammatory response is induced with cytokines (FIG. 2).

FIG. 2 provides a graphical representation of data of human pancreatic beta-cells treated with cytokines and microvesicles. The graph illustrates the differences in the apoptotic affects of each treatment.

MV were determined to have a concentration of $5.85 \times 10e11$ particles/mL. Most of these particles had major peak sizes of 94 and 128 nm, being in the 20-200 nm range of known vesicle sizes in other bacterial species. SDS-PAGE of *Lactobacillus johnsonii* CM and MV illustrated differences in banding pattern. Mass spectroscopy data confirmed MV contained certain specific or more abundant proteins than the CM. In HPB, MV showed a reduction in the amount of apoptotic and pre-apoptotic cells when exposed with cytokines compared to HPB exposed only to cytokines or to MV. A mechanism in which *Lactobacillus johnsonii* not only provides probiotic and immunological effects to the host's gut but systemically to the HPB, potentially reducing proinflammatory responses has been identified. MVs transform the way we view probiotic-host interactions.

Although the present invention has been described in considerable detail with reference to certain preferred versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C § 112, sixth paragraph. In particular, the use of "step of" in the claims herein is not intended to invoke the provisions of 35 U.S.C § 112, sixth paragraph.

What is claimed is:

1. A method for treating or Type-1 diabetes, comprising: administering to a subject in need thereof, a composition comprising an effective amount of microvesicles purified from *Lactobacillus johnsonii*, wherein the subject exhibits a fasting blood sugar level of at least 100 mg/dL.

2. The method of claim 1, wherein *Lactobacillus johnsonii* comprises *Lactobacillus johnsonii* N6.2.

3. The method of claim 1, wherein the composition inhibits apoptosis in beta cells in the subject.

4. The method of claim 1, wherein the oral administrating occurs prior to the onset of type-1 diabetes.

5. The method of claim 1, wherein the subject exhibits a cytokine-induced pro-inflammatory response, the composition inhibits apoptosis of beta cells.

\* \* \* \* \*